(12) United States Patent
Kruk et al.

US010473660B2

(10) Patent No.: US 10,473,660 B2
(45) Date of Patent: Nov. 12, 2019

(54) MATERIALS AND METHODS FOR DETECTING CANCER BASED ON URINARY LEVELS OF RHAMM

(71) Applicants: Patricia Ann Kruk, Tampa, FL (US); Stephanie Tania Buttermore, Tampa, FL (US)

(72) Inventors: Patricia Ann Kruk, Tampa, FL (US); Stephanie Tania Buttermore, Tampa, FL (US)

(73) Assignee: UNIVERSITY OF SOUTH FLORIDA, Tampa, FL (US)

( * ) Notice: Subject to any disclaimer, the term of this patent is extended or adjusted under 35 U.S.C. 154(b) by 0 days.

(21) Appl. No.: 16/023,496

(22) Filed: Jun. 29, 2018

(65) Prior Publication Data

US 2018/0306793 A1    Oct. 25, 2018

Related U.S. Application Data

(63) Continuation of application No. PCT/US2017/018596, filed on Feb. 20, 2017.

(60) Provisional application No. 62/296,832, filed on Feb. 18, 2016.

(51) Int. Cl.
*G01N 33/50* (2006.01)
*G01N 33/574* (2006.01)

(52) U.S. Cl.
CPC . *G01N 33/57411* (2013.01); *G01N 33/57419* (2013.01); *G01N 33/57449* (2013.01); *G01N 2333/70596* (2013.01); *G01N 2800/52* (2013.01)

(58) Field of Classification Search
CPC ..... G01N 2800/52; G01N 2333/70596; G01N 33/57449; G01N 33/57419; G01N 33/57411
See application file for complete search history.

(56) References Cited

U.S. PATENT DOCUMENTS

| | | |
|---|---|---|
| 2003/0170755 A1* | 9/2003 | Schmitt ................ C07K 14/47 435/7.23 |
| 2009/0181384 A1 | 7/2009 | Nekarda et al. |
| 2010/0062000 A1 | 3/2010 | Turley et al. |
| 2011/0262921 A1 | 10/2011 | Sabichi et al. |
| 2013/0217015 A1 | 8/2013 | Nicosia et al. |
| 2017/0292963 A1* | 10/2017 | Worley ................ G01N 33/566 |

FOREIGN PATENT DOCUMENTS

WO   WO-2015027779 A1 *  3/2015  ....... G01N 33/57484

OTHER PUBLICATIONS

RayBiotech, Inc. "RayBio Custom ELISA Kit Preliminary Manual." Protocol Document. 2013. (Year: 2013).*

The American College of Obstetricians and Gynecologists Committee on Gynecologic Practice and the Practice Committee of the American Society from Reproductive Medicine, "Female age-related fertility decline," *Fertility and Sterility*, Mar. 2014, 101(3):633-634, Elsevier Inc.

Au-Yeung, G. et al., "Impact of obesity on chemotherapy dosing for women with advanced stage serous ovarian cancer in the Australian Ovarian Cancer Study (AOCS)," *Gynecologic Oncology*, 2014, 133:16-22, Elsevier Inc.

Bae, H. S. et al., "Obesity and epithelial ovarian cancer survival: a systematic review and meta-analysis," *Journal of Ovarian Research*, 2014, 7(41):1-8.

Basso, B. et al., "IL-1b, IL-6 and IL-8 levels in gyneco-obstetric infections," *Infectious Diseases in Obstetrics and Gynecology*, Dec. 2005, 13(4):207-211, Taylor & Francis.

Bogush, T. A. et al., Immunofluorescent Assay of ERCC1 and Estimation of Clinical Significance of the Protein Expression in Ovarian Cancer Tissue, *Biochemistry and Biophysics*, 2014, 457:141-145, Pleiades Publishing.

Bourgeois, M. et al., "Gender-specific differences in the urinary expression of aldosterone, IL-1α and IL-1β," *Biomarkers Med.*, 2010 4(6):843-847, Future Medicine Ltd.

Brändstedt, J. et al., "Anthropometric factors and ovarian cancer risk in the Malmö Diet and Cancer Study," *Cancer Epidemiology*, 2011, 35:432-437, Elsevier Ltd.

Browne, A. et al., "Differential expression of IL-8 and IL-8 receptors in benign, borderline and malignant ovarian epithelial tumours," *Cytokine*, 2013, 64:413-421, Elsevier Ltd.

Burney, R. O. et al., "Pathogenesis and pathophysiology of endometriosis," *Fertility and Sterility*, Sep. 2012, 98(3):511-519, Elsevier Inc.

Caillaud, M. et al., "In vivo effect of interleukin-1beta and interleukin-1RA on oocyte cytoplasmic maturation, ovulation, and early embryonic development in the mare," *Reproductive Biology and Endocrinology*, 2005, 3(26):1-9.

Califano, D. et al., "High HMGA2 Expression and High Body Mass Index Negatively Affect the Prognosis of Patients With Ovarian Cancer," *Journal of Cellular Physiology*, 2014, 229:53-59, 2013 Wiley Periodicals, Inc.

Canchola, A. J. et al., "Body size and the risk of ovarian cancer by hormone therapy use in the California Teachers Study cohort," *Cancer Causes Control*, Dec. 2010, 21(12):2241-2248, Springer Science+Business Media B.V.

Carlson, K. J. et al., "Screening for Ovarian Cancer," *Ann Intern Med.*, 1994, 121:124-132, American College of Physicians.

(Continued)

*Primary Examiner* — Christopher Adam Hixson
(74) *Attorney, Agent, or Firm* — Saliwanchik, Lloyd & Eisenschenk

(57) ABSTRACT

The invention pertains to diagnosis and treatment of ovarian cancer (OC), cervical cancer (CC), or colorectal cancer (CRC). One embodiment of the invention provides a method of identifying OC, CC, or CRC based on the level of RHAMM in the urine of a subject. Another embodiment of the invention provides a method of identifying OC based on the level of RHAMM in the urine and CA125 in the blood of a subject. The invention also pertains to monitoring the efficacy of a treatment of OC, CC, or CRC based on the level of RHAMM protein in the urine and/or the level of CA125 in the blood. Another embodiment of the invention provides devices and reagents to assay RHAMM in a urine sample and optionally, assay CA125 in a blood sample.

16 Claims, 10 Drawing Sheets

(56) References Cited

OTHER PUBLICATIONS

Chae, J. S. et al., "Mild weight loss reduces inflammatory cytokines, leukocyte count, and oxidative stress in overweight and moderately obese participants treated for 3 years with dietary modification," *Nutrition Research*, 2013, 33:195-203, Elsevier Inc.

Collaborative Group on Epidemiological Studies of Ovarian Cancer, "Ovarian Cancer and Body Size: Individual Participant Meta-Analysis Including 25,157 Women with Ovarian Cancer from 47 Epidemiological Studies," *PLoS Medicine*, Apr. 2012, 9(4):1-12.

Corwin, E. J. et al., "Interleukin-1β Elevation During the Postpartum Period," *Annuals of Behavioral Medicine*, 2003, 25(1):41-47, The Society of Behavioral Medicine.

Corwin, E. J. et al., "Symptoms of Postpartum Depression Associated With Elevated Levels of Interleukin-1 Beta During the First Month Postpartum," *Biological Research for Nursing*, Oct. 2008, 10(2):128-133, Sage Publications.

Cragun, J. M., "Screening for Ovarian Cancer," *Cancer Control*, Jan. 2011, 18(1):16-21.

Delort, L. et al., "Central Adiposity as a Major Risk Factor of Ovarian Cancer," *Anticancer Research*, 2009, 29:5229-5234.

Diaz, E. S. et al., "Obesity-associated adipokines correlate with survival in epithelial ovarian cancer," *Gynecologic Oncology*, 2013, 129:353-357, Elsevier Inc.

Dinarello, C. A., "Immunological and Inflammatory Functions of the Interleukin-1 Family," *Annu. Rev. Immunol.*, 2009, 27:519-550, Annual Reviews.

Dinarello, C. A., "The paradox of pro-inflammatory cytokines in cancer," *Cancer Metastasis Rev*, 2006, 25:307-313, Springer + Business Media, LLC.

Dobrzycka, B. et al., "Serum levels of IL-6, IL-8 and CRP as prognostic factors in epithelial ovarian cancer," *Eur. Cytokine Netw.*, 2013, 24(3):106-113.

Donath, M. Y. et al., "Inflammation in Obesity and Diabetes: Islet Dysfunction and Therapeutic Opportunity," *Cell Metabolism*, Jun. 4, 2013, 17:860-872, Elsevier Inc.

Engeland, A. et al., "Height, Body Mass Index, and Ovarian Cancer: A Follow-Up of 1.1 Million Norwegian Women," *Journal of the National Cancer Institute*, Aug. 20, 2003, 95(16):1244-1248, Oxford University Press.

Fabian, C. et al., "Protein profiles in human ovarian cancer cell lines correspond to their metabolic activity and to metabolic profiles of respective tumor xenografts," *FEBS Journal*, 2012, 279:882-891, The Authors Journal compilation.

Field, K. M. et al., "Chemotherapy Dosing Strategies in the Obese, Elderly, and Thin Patient: Results of a Nationwide Survey," *Journal of Oncology Practice*, May 2008, 4(3):108-113, American Society of Clinical Oncology.

Gabrielson, M. et al., "Expression of Mitochondrial Regulators PGC1α and TFAM as Putative Markers of Subtype and Chemoresistance in Epithelial Ovarian Carcinoma," *PLoS One*, Sep. 2014, 9(9):1-10.

Gerard, N. et al., "The interleukin-1 system and female reproduction," *Journal of Endocrinology*, 2004, 180:203-212, Society of Endocrinology.

Hefler-Frischmuth, K. et al., "Serum C-reactive protein in the differential diagnosis of ovarian masses," *European Journal of Obstetrics & Gynecology and Reproductive Biology*, 2009, 147:65-68, Elsevier Ireland Ltd.

Hjerpe, E. et al., "Metabolic Markers and HSP60 in Chemonaive Serous Solid Ovarian Cancer Versus Ascites," *International Journal of Gyecological Cancer*, Oct. 2014, 24(8):1389-1394, IGCS and ESGO.

Hong, M. et al., "Urinary Macrophage Migration Inhibitory Factor Serves as a Potential Biomarker for Acute Kidney Injury in Patients with Acute Pyelonephritis," *Mediators of Inflammation*, 2012, 2012(381358):1-9, Hindawi Publishing Corporation.

Hotamisligil, G. S., "Inflammation and metabolic disorders," *Nature*, Dec. 14, 2006, 444:860-867, Nature Publishing Group.

Jakimovska, M. et al., "Circulating serum sVCAM-1 concentration in advanced ovarian cancer patients: correlation with concentration in ascites," *Radiol Oncol*, 2014, 48(3):307-313.

Kisielewski, R. et al., "Inflammation and ovarian cancer—current views," *Ginekol Pol.*, 2013, 84:293-297.

Kodama, J. et al., "Serum C-reactive protein as a prognostic lnctor in patients with epithelial ovarian cancer," *European Journal of Obstetrics & Gynecology and Reproductive Biology*, 1999, 82:107-110, Elsevier Science, Ltd.

Kotsopoulos, J. et al., "Anthropometric measures and risk of epithelial ovarian cancer: results from the Nurses' Health Study," *Obesity (Silver Springs)*, Aug. 2010, 18(8):1625-1631.

Kotsopoulos, J. et al., "Height, weight, BMI and ovarian cancer survival," *Gynecologic Oncology*, 2012, 127:83-87, Elsevier Inc.

Leitzmann, M. F. et al., "Body mass index and risk of ovarian cancer," *Cancer*, Feb. 15, 2009, 115(4):812-822.

Lewis, A. M. et al., "Interleukin-I and cancer progression: the emerging role of interleukin-I receptor antagonist as a novel therapeutic agent in cancer treatment," *Journal of Translational Medicine*, 2006, 4(48):1-12.

Lim, D. et al, "Precursors and pathogenesis of ovarian carcinoma," *Pathology*, Apr. 2013, 45(3):229-242, Royal College of Pathologists of Australasia.

Macció, A. et al., "Inflammation and ovarian cancer," *Cytokine*, 2012, 58:133-147, Elsevier Ltd.

Maedler, K. et al., "Leptin modulates β cell expression of IL-1 receptor antagonist and release of IL-1 β in human islets," *PNAS*, May 25, 2004, 101(21):8138-8143, The National Academy of Sciences of the USA.

Makowski, L. et al., "Obesity increases tumor aggressiveness in a genetically engineered mouse model of serous ovarian cancer," *Gynecologic Oncology*, 2014, 133:90-97, Elsevier Inc.

Malek, A. et al., "HMGA2 gene is a promising target for ovarian cancer silencing therapy," *International Journal of Cancer*, 2008, 123:348-356, Wiley-Liss, Inc.

Mantovani, A. et al., "Cancer-related inflammation," *Nature*, Jul. 24, 2008, 454:436-444, Macmillan Publishers Ltd.

McGee, J. et al., "Anthropometric Measures and Risk of Ovarian Cancer Among BRCA1 and BRCA2 Mutation Carriers," *Obesity*, Jun. 2012, 20(6):1288-1292.

McGettrick, A. F. et al., "NLRP3 and IL-1β in macrophages as critical regulators of metabolic diseases," *Diabetes, Obesity and Metabolism*, 2013, 15(3):19-25, John Wiley & Sons Ltd.

Moiseyenko, V. M. et al., "Evidence for clinical efficacy of mitomycin C in heavily pretreated ovarian cancer patients carrying germ-line BRCA1 mutation," *Med Oncol*, 2014, 31:1-6, Springer Science+Business Media.

Mustea, A. et al., "Decreased IL-1 RA concentration in ascites is associated with a significant improvement in overall survival in ovarian cancer," *Cytokine*, 2008, 42:77-84, Elsevier Ltd.

Nguyen, L. et al., "Biomarkers for early detection of ovarian cancer," *Women's Health*, 2013, 9(2):171-187, Future Medicine Ltd.

Okamoto, T. et al., "Hepatocyte Nuclear Factor-1β (HNF-1β) Promotes Glucose Uptake and Glycolytic Activity in Ovarian Clear Cell Carcinoma," *Molecular Carcinogenesis*, 2015, 54:35-49, Wiley Periodicals, Inc.

Olsen, C. M. et al., "Obesity and risk of ovarian cancer subtypes: evidence from the Ovarian Cancer Association Consortium," *Endocr Relat Cancer*, Apr. 2013, 20(2):1-19.

Pereira, A. B. et al., Urinary chemokines and anti-inflammatory molecules in renal transplanted patients as potential biomarkers of graft function: a prospective study, *Int Urol Nephrol*, 2012, 44:1539-1548, Springer Science+Business Media, B.V.

Pruijm, M. et al., "Not All Inflammatory Markers Are Linked to Kidney Function: Results from a Population-Based Study," *American Journal of Nephrology*, 2012, 35:288-294, S. Karger AG.

Schouten, L. J. et al., "Height, Body Mass Index, and Ovarian Cancer," *Cancer Epidemiol Biomarkers Prev.*, Apr. 2008, 17(4):902-912.

Spranger, J. et al., "Inflammatory Cytokines and the Risk of Develop Type 2 Diabetes," *Diabetes*, Mar. 2003, 52:1-6.

Su, Z. et al., "Detection and monitoring of ovarian cancer," *Clinica Chimica Acta*, 2013, 415:341-345, Elsevier B.V.

Vassiliadis, S. et al., "Endometriosis and infertility: A multicytokine imbalance versus ovulation, fertilization and early embryo

(56) References Cited

OTHER PUBLICATIONS development," *Clinical & Developmental Immunology*, Jun. 2005, 12(2):125-129, Taylor & Francis Group Ltd.

Vural, P. et al., "Effects of hormone replacement therapy of plasma pro-inflammatory and anti-inflammatory cytokines and some bone turnover markers in postmenopausal women," *Pharmacological Research*, 2006, 54:298-302, Elsevier Ltd.

WHO Technical Report Series 894, "Obesity: Preventing and Managing the Global Epidemic," World Health Organization, 2000, Geneva.

Zhou, Y. et al., "Body mass index, physical activity, and mortality in women diagnosed with ovarian cancer: Results from the Women's Health Initiative," *Gynecologic Oncology*, 2014, 133:4-10, Elsevier. Inc.

International Search Report in International Application No. PCT/US2017/018596, filed Feb. 20, 2017.

Greiner, J. et al., "Receptor for hyaluronan acid-mediated motility (RHAMM) is a new immunogenic leukemia-associated antigen in acute and chronic myeloid leukemia," *Experimental Hematology*, 2002, 30:1029-1035, Elsevier Science Inc.

Kouba, E.J. et al., "Clinical use of serum CA-125 levels in patients undergoing radical cystectomy for transitional cell carcinoma of the bladder," *Urologic Oncology: Seminars and Original Investigations*, 2009, 27:486-490, Elsevier Inc.

Villegas-Ruíz, V. et al., "A case of cervical cancer expressed three mRNA variant of Hyaluronan-mediated motility receptor," *International Journal of Clinical and Experimental Pathology*, May 1, 2014, 7(5):2256-2264.

Yu, J. et al., "A Novel Set of DNA Methylation Markers in Urine Sediments for Sensitive/Specific Detection of Bladder Cancer", *Clin Cancer Res*, Dec. 15, 2007, 13(24):7296-7304, American Association for Cancer Research.

Walczak, H. et al., "The CD95 (APO-1/Fas) and the TRAIL (APO-2L) Apoptosis Systems", *Experimental Cell Research*, 2000, 256:58-66, Academic Press.

Thomenius, M.J. et al., "Bcl-2 on the endoplasmic reticulum: protecting the mitochondria from a distance", *Journal of Cell Science*, 2003, 116(22):4493-4499, The Company of Biologists Ltd.

Sutphen, R. et al., "Lysophospholipids Are Potential Biomarkers of Ovarian Cancer", *Cancer Epidemiology, Biomarkers & Prevention*, 2004, 13(7):1185-1191, American Association for Cancer Research.

Smith, S.D. et al., "Urine Detection of Survivin and Diagnosis of Bladder Cancer", *JAMA*, Jan. 17, 2001, 285(3):324-328, American Medical Association.

Sauter, E.R. et al., "Prostate-specific antigen and insulin-like growth factor binding protein-3 in nipple aspirate fluid are associated with breast cancer", *Cancer Detection and Prevention*, 2002, 26, 149-157, Elsevier Science Ltd.

Sagarra, R.A.M. et al., "P53 and Bcl-2 as prognostic predictors in epithelial ovarian cancer", *International Journal of Gynecological Cancer*, 2002, 12:720-727, IGCS.

Petricoin, E.F. et al., "Use of proteomic patterns in serum to identify ovarian cancer", *The Lancet*, Feb. 16, 2002, 359:572-577, The Lancet Publishing Group.

Nör, J.E. et al., "Up-Regulation of Bcl-2 in Microvascular Endothelial Cells Enhances Intratumoral Angiogenesis and Accelerates Tumor Growth", *Cancer Research*, Mar. 1, 2001, 61:2183-2188, American Association for Cancer Research.

Nakase, K. et al., "Elevated levels of soluble interleukin-2 receptor in serum of patients with hematological or non-hematological malignancies", *Cancer Detection and Prevention*, 2005, 29:256-259, Elsevier Ltd.

Nagata, S., "Apoptotic DNA Fragmentation", *Experimental Cell Research*, 2000, 256:12-18, Academic Press.

Lowe, S.W. et al., "Apoptosis in cancer", *Carcinogenesis*, 2000, 21(3):485-495, Oxford University Press.

Loeffler, M. et al., "The Mitochondrion in Cell Death Control: Certainties and Incognita", *Experimental Cell Research*, 2000, 256:19-26, Academic Press.

Lickliter, J.D. et al., "HA14-1 selectively induces apoptosis in Bcl-2-overexpressing leukemia/lymphoma cells, and enhances cytarabine-induced cell death", *Leukemia*, 2003, 17:2074-2080, Nature Publishing Group.

Khalifeh, I. et al., "Expression of Cox-2, CD34, Bcl-2, and p53 and Survival in Patients with Primary Peritoneal Serous Carcinoma and Primary Ovarian Serous Carcinoma", *International Journal of Gynecological Pathology*, Apr. 2004, 23(2):162-169, Lippincott Williams & Wilkins, Baltimore.

Jemal, A. et al., "Cancer Statistics, 2008", *CA Cancer J Clin*, Mar./Apr. 2008, 58(2):71-96, American Cancer Society, Inc.

Iervolino, A. et al., "Bcl-2 overexpression in human melanoma cells increases angiogenesis through VEGF mRNA stabilization and HIF-1-mediated transcriptional activity", *The FASEB Journal*, Jul. 1, 2002, 1-22.

Hazelton, D. et al., "Vascular Endothelial Growth Factor Levels in Ovarian Cyst Fluid Correlate with Malignancy", *Clinical Cancer Research*, Apr. 1999, 5:823-829, American Association for Cancer Research.

Friedrich, M.G. et al., "Detection of Methylated Apoptosis-Associated Genes in Urine Sediments of Bladder Cancer Patients", *Clinical Cancer Research*, Nov. 15, 2004, 10:7457-7465, American Association for Cancer Research.

Farrow, S.N. et al., "New members of the Bcl-2 family and their protein partners", *Current Opinion in Genetics & Development*, 1996, 6:45-49, Current Biology Ltd.

Cao, Y. et al., "Elevated levels of urine angiostatin and plasminogen/plasmin in cancer patients", *International Journal of Molecular Medicine*, 2000, 5:547-551.

Badgwell, D. et al., "Urinary mesothelin provides greater sensitivity for early stage ovarian cancer than serum mesothelin, urinary hCG free beta subunit and urinary hCG beta core fragment", *Gynecologic Oncology*, 2007, 106:490-497, Elsevier Inc.

Ackermann, E.J. et al., "The Role of Antiapoptotic Bcl-2 Family Members in Endothelial Apoptosis Elucidated with Antisense Oligonucleotides", *The Journal of Biological Chemistry*, Apr. 16, 1999, 274(16):11245-11252, The American Society for Biochemistry and Molecular Biology, Inc., U.S.A.

Lu, K.H. et al., "Selection of Potential Markers for Epithelial Ovarian Cancer with Gene Expression Arrays and Recursive Descent Partition Analysis", *Clinical Cancer Research*, May 15, 2004, 10:3291-3300, American Association for Cancer Research.

Lawrence, H.P., "Salivary Markers of Systemic Disease: Noninvasive Diagnosis of Disease and Monitoring of General Health", *Journal of the Canadian Dental Association*, Mar. 2002, 68(3):170-174, J Can Dent Assoc.

Jandu, N. et al., "Human ovarian cancer ascites fluid contains a mixture of incompletely degraded soluble products of fibrin that collectively possess an antiangiogenic property", *International Journal of Gynecological Cancer*, 2006, 16:1536-1544, IGCS and ESGO.

Holash, J. et al., "New model of tumor angiogenesis: dynamic balance between vessel regression and growth mediated by angiopoietins and VEGF", *Oncogene*, 1999, 18:5356-5362, Stockton Press.

Fuhrmann-Benzakein, E. et al., "Elevated Levels of Angiogenic Cytokines in the Plasma of Cancer Patients", *Int. J. Cancer*, 2000, 85:40-45, Wiley-Liss, Inc., the International Union Against Cancer.

Folkman, J., "Fighting Cancer by Attacking Its Blood Supply", *Scientific American*, Sep. 1996, 150-154.

Ferrara, N., "Vascular Endothelial Growth Factor: Basic Science and Clinical Progress", *Endocrine Reviews*, 2004, 25(4):581-611, The Endocrine Society, U.S.A.

Bast, R.C. et al., "New tumor markers: CA125 and beyond", *International Journal of Gynecological Cancer*, 2005, 15(Suppl. 3):274-281, IGCS.

Anderson, N.S. et al., "Urinary levels of Bcl-2 are elevated in ovarian cancer patients", *Gynecologic Oncology*, 2009, 112:60-67, 2008 Elsevier Inc.

Alvarez Secord, A. et al., "The relationship between serum vascular endothelial growth factor, persistent disease, and survival at second-look laparotomy in ovarian cancer", *Gynecologic Oncology*, 2004, 94:74-79, Elsevier Inc.

(56) References Cited

OTHER PUBLICATIONS

Zhang, Z. et al., "Combining multiple serum tumor markers improves detection of stage I epithelial ovarian cancer", *Gynecologic Oncology*, 2007, 107:526-531, Elsevier Inc.

Yokoyama, Y. et al., "Synergy between Angiostatin and Endostatin: Inhibition of Ovarian Cancer Growth", *Cancer Research*, Apr. 15, 2000, 60:2190-2196, American Association for Cancer Research.

Yokoyama, Y. et al., "Endostatin Binding to Ovarian Cancer Cells Inhibits Peritoneal Attachment and Dissemination", *Cancer Res*, Nov. 15, 2007, 67(22):10813-10822, American Association for Cancer Research.

Sowter, H.M. et al., "Hepatocyte Growth Factor (HGF) in Ovarian Epithelial Tumour Fluids Stimulates the Migration of Ovarian Carcinoma Cells", *Int. J. Cancer*, 1999, 83:476-480, Wiley-Liss, Inc., International Union Against Cancer.

Rubatt, J.M. et al., "Independent prognostic relevance of microvessel density in advanced epithelial ovarian cancer and associations between CD31, CD105, p53 status, and angiogenic marker expression: A Gynecologic Oncology Group study", *Gynecologic Oncology*, 2009, 112:469-474, Elsevier Inc.

Rosen, D.G. et al., "Potential markers that complement expression of CA125 in epithelial ovarian cancer", *Gynecologic Oncology*, 2005, 99:267-277, Elsevier Inc.

Persano, L. et al., "Anti-angiogenic gene therapy of cancer: Current status and future prospects", *Molecular Aspects of Medicine*, 2007, 28:87-114, Elsevier Ltd.

Perri, S.R. et al., "Plasminogen Kringle 5 blocks tumor progression by antiangiogenic and proinflammatory pathways", *Mol Cancer Ther*, Feb. 2007, 6(2):441-449, American Association for Cancer Research.

Nicosia, S.V. et al., "Cytology of Human Ovarian Surface Epithelial Brushings", *Cancer (Cancer Cytopathol)*, 2004, 102:1-10, 2003 American Cancer Society.

Murthi, P. et al., "Plasminogen fragmentation and increased production of extracellular matrix-degrading proteinases are associated with serous epithelial ovarian cancer progression", *Gynecologic Oncology*, 2004, 92:80-88, 2003 Elsevier Inc.

Moore, R.G. et al., "The use of multiple novel tumor biomarkers for the detection of ovarian carcinoma in patients with a pelvic mass", *Gynecologic Oncology*, 2008, 108:402-408, 2007 Elsevier Inc.

\* cited by examiner

MATERIALS AND METHODS FOR DETECTING CANCER BASED ON URINARY LEVELS OF RHAMM

CROSS-REFERENCE TO RELATED APPLICATIONS

This application is a continuation of International Patent Application No. PCT/US2017/018596, filed Feb. 20, 2017, which claims the benefit of U.S. Provisional Application Ser. No. 62/296,832, filed Feb. 18, 2016, the disclosures of each of which are incorporated herein by reference in their entirety.

BACKGROUND OF THE INVENTION

Ovarian cancer (OC) has the highest mortality among gynecological cancers. The lack of early symptoms and the absence of a reliable screening test to detect OC results in over 70% of women being diagnosed after the disease has spread beyond ovary. Late diagnosis of OC drastically decreases 5-year survival rate from about 90% to less than 50%. Therefore, the prognosis for OC is poor with approximately 12,000 deaths annually and 5-year survival of less than 37%.

Currently, physical pelvic examination, ultrasound examination, and blood levels of CA125 are used for detection of OC. However, none of these methods provides a consistent detection. For example, while over 80% of women with OC have elevated blood levels of CA125, blood levels of CA125 are only about 50% accurate in detecting early stage OC. Therefore, poor prognosis associated with OC results from late detection and lack of screening methods to detect OC.

BRIEF SUMMARY OF THE INVENTION

Minimal expression of Receptor for Hyaluronan-mediated motility (RHAMM) is detected in normal tissues; however, RHAMM it is elevated in certain cancers. The invention provides that RHAMM protein is elevated in urine samples from subjects having OC, cervical cancer (CC), and colorectal cancer (CRC) when compared to urine samples from healthy subjects.

Accordingly, one embodiment of the invention provides materials and methods for identifying OC, CC, or CRC based on the level of RHAMM in a urine sample obtained from a subject. Another embodiment of the invention also provides materials and methods for identifying OC based on the level of RHAMM in a urine sample and the level of CA125 in a blood sample obtained from a subject.

In a further embodiment, the invention provides methods for identifying OC, CC, or CRC based on the level of RHAMM in a urine sample and/or the level of CA125 in a blood sample obtained from a subject and optionally, treating OC, CC, or CRC by administering a therapy.

The invention further provides devices and reagents to quantify the combination of RHAMM and CA125.

DETAILED DISCLOSURE OF THE INVENTION

Figure 1A:
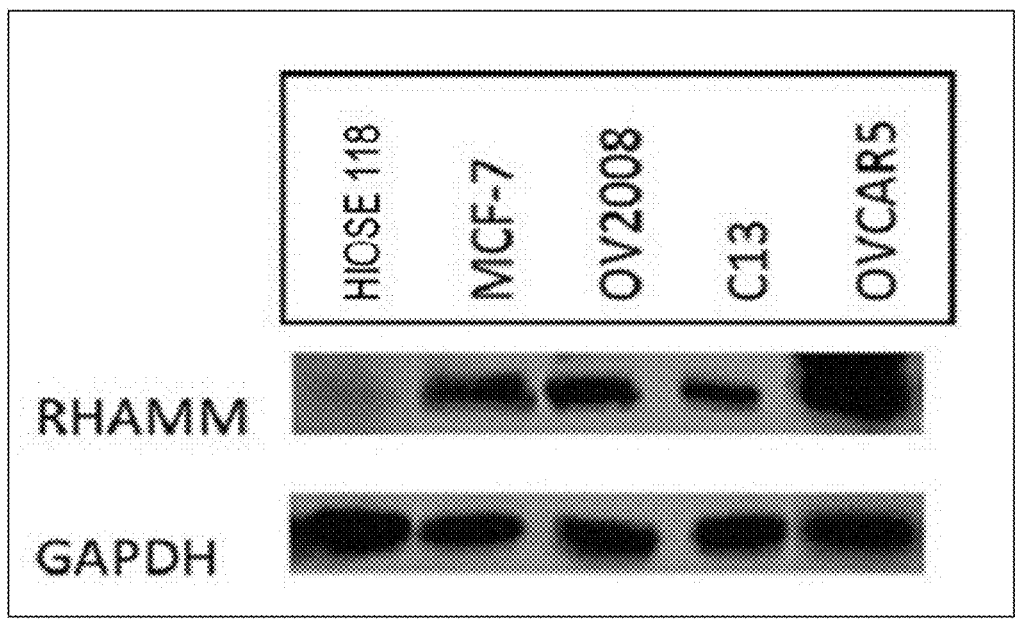
FIGS. 1A-1B. RHAMM is overexpressed in OC cell protein lysate and conditioned medium compared to normal OSE. Breast cancer cell line (MCF-7) is used as positive control. $p<0.05$.
Figure 1B:
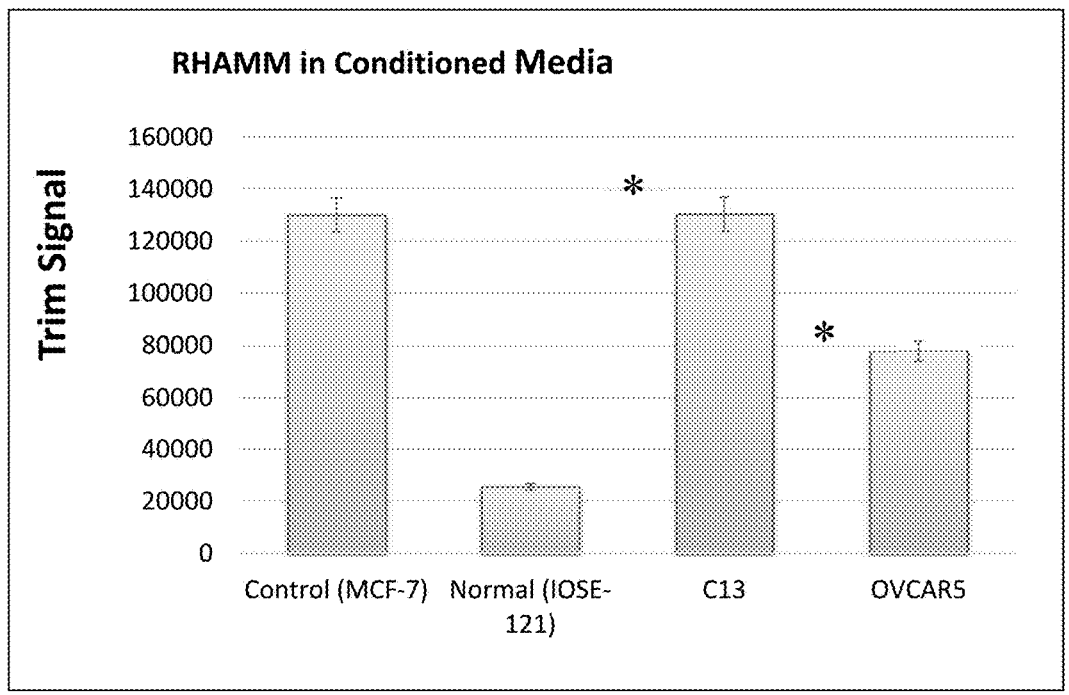
Figure 2:
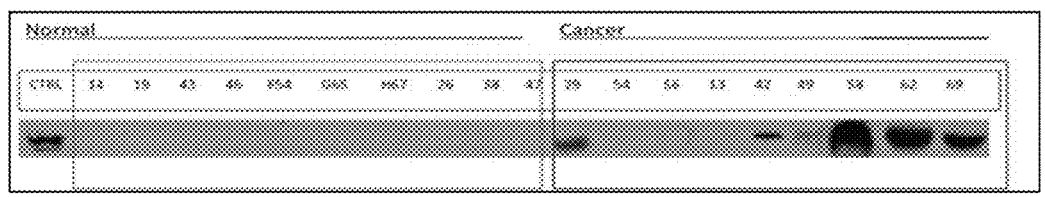
FIG. 2. RHAMM levels are consistently higher in urine from OC subjects (n=10) compared to urine from normal subjects (n=10).
Figure 3A:
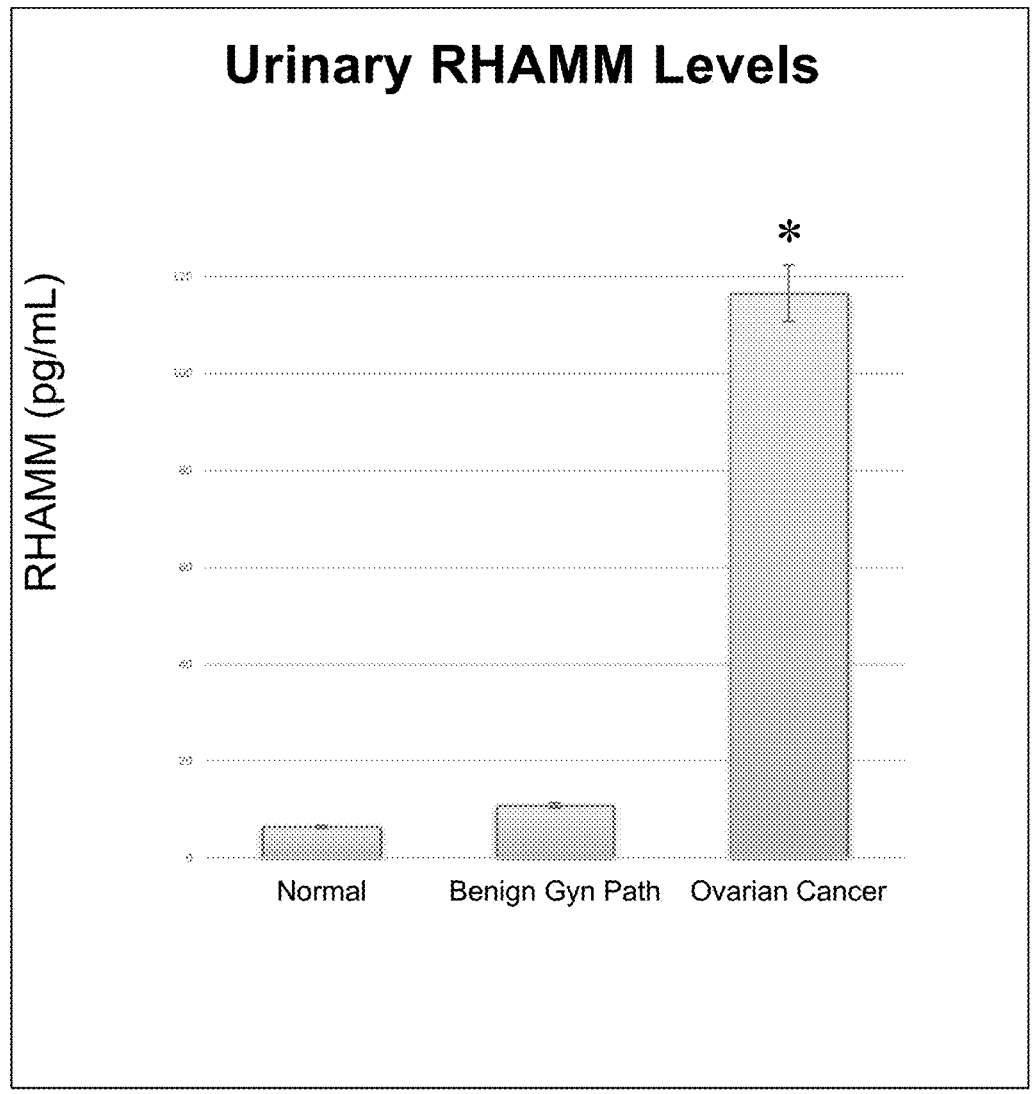
FIGS. 3A-3B. Urinary RHAMM protein expression is significantly higher in OC. Urine from healthy subjects (n=29) or subjects having: benign gynecological disease (n=30), OC (n=126), cervical cancer (n=21), colorectal cancer (n=9), breast cancer (n=20), brain cancer (n=20), head and neck cancer (n=20), lung cancer (n=20), sarcoma (n=19), endometrial cancer (n=20), bladder cancer (n=12), and prostate cancer (n=14) was analyzed for RHAMM levels. * indicates $p<0.05$.
Figure 3B:
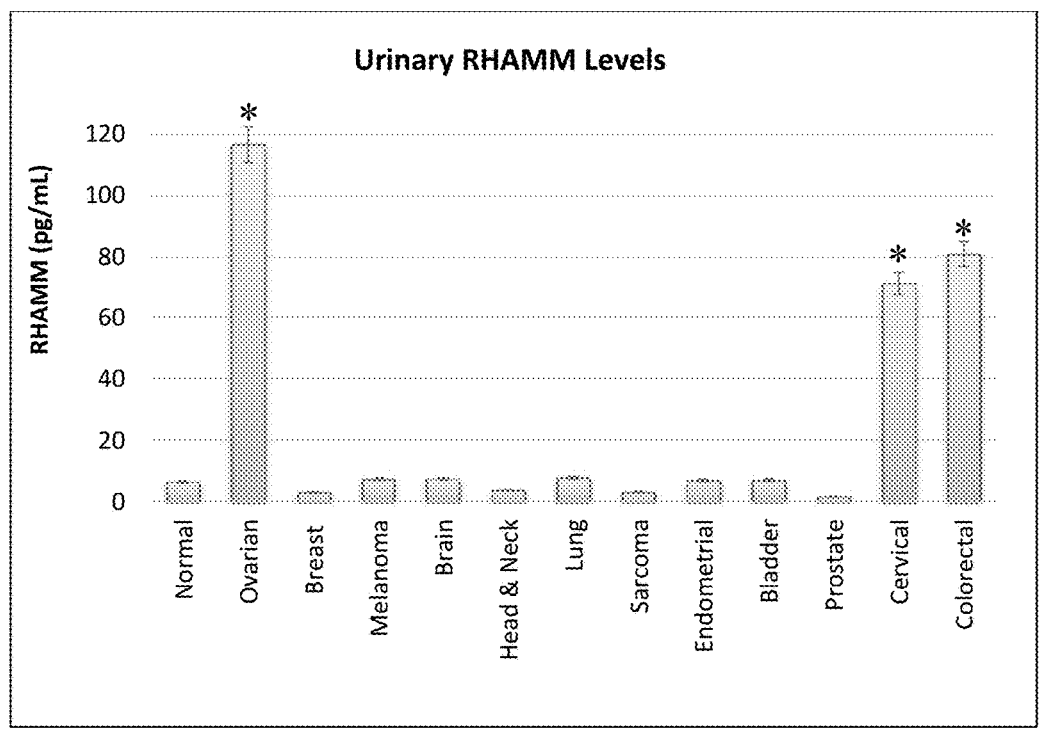
Figure 4A:
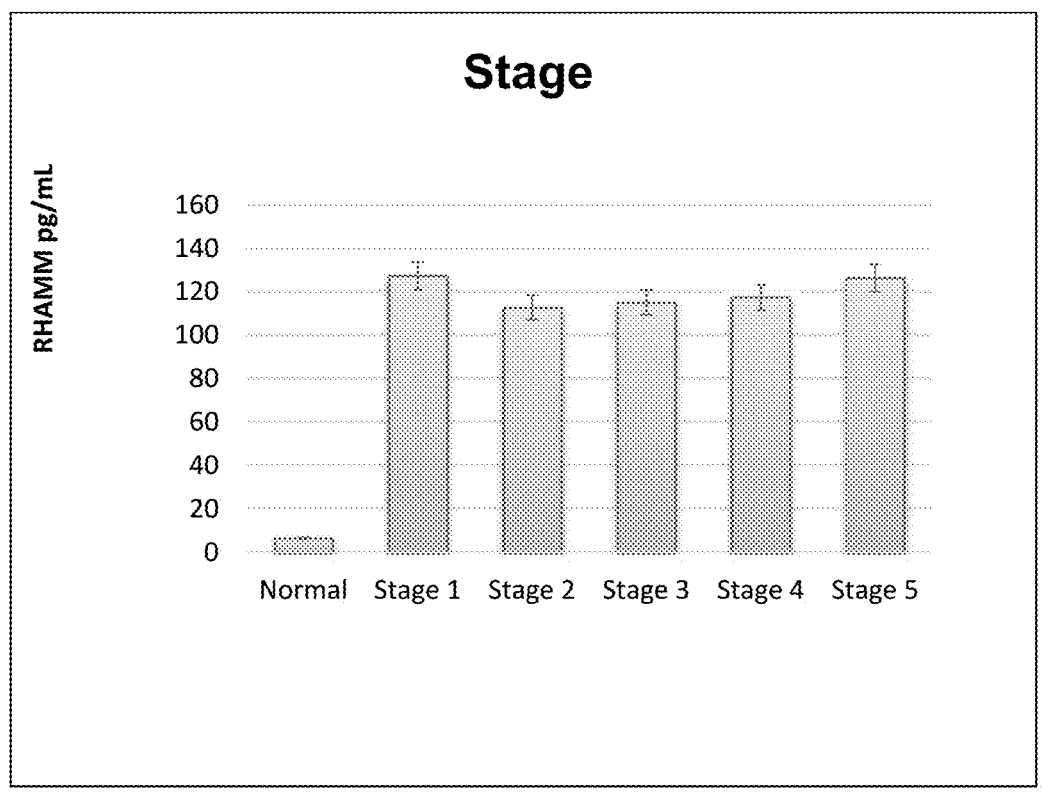
FIGS. 4A-4B. Urinary RHAMM expression is similar regardless of stage or grade in OC. Urine from healthy subjects (n=29) or subjects having or subjects having OC at stage 1 (n=11), stage 2 (n=2), stage 3 (n=45), stage 4 (n=6), stage 5 (n=11), low grade (n=23) and high grade (n=27) was analyzed for RHAMM levels.
Figure 4B:
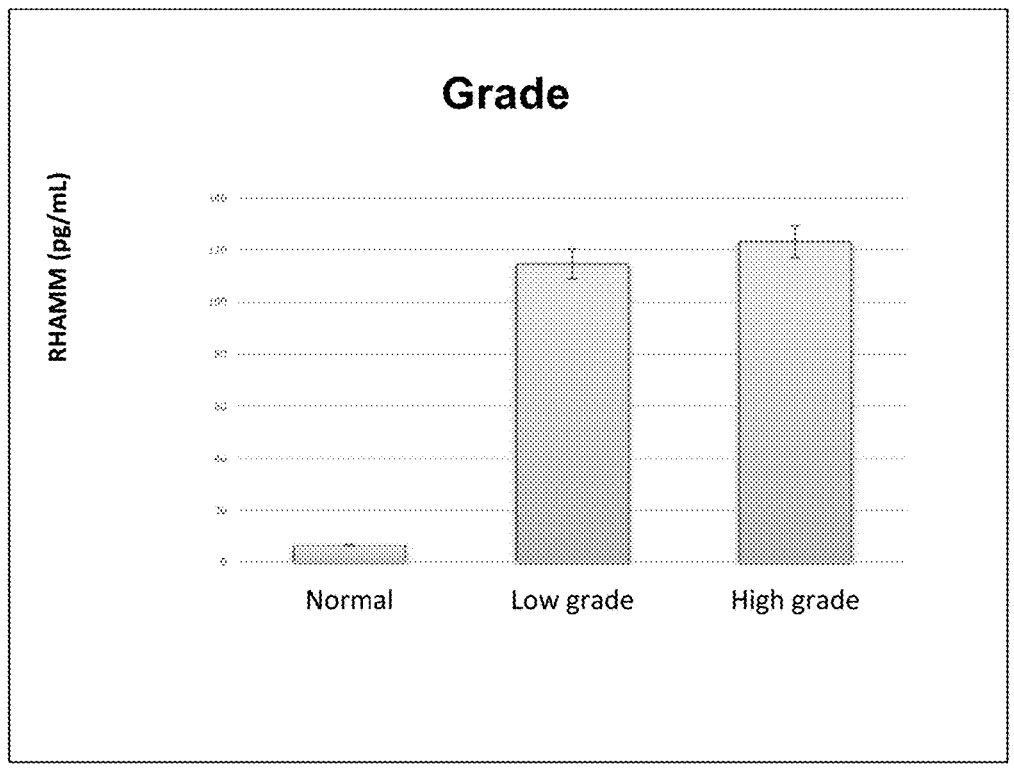
Figure 5:
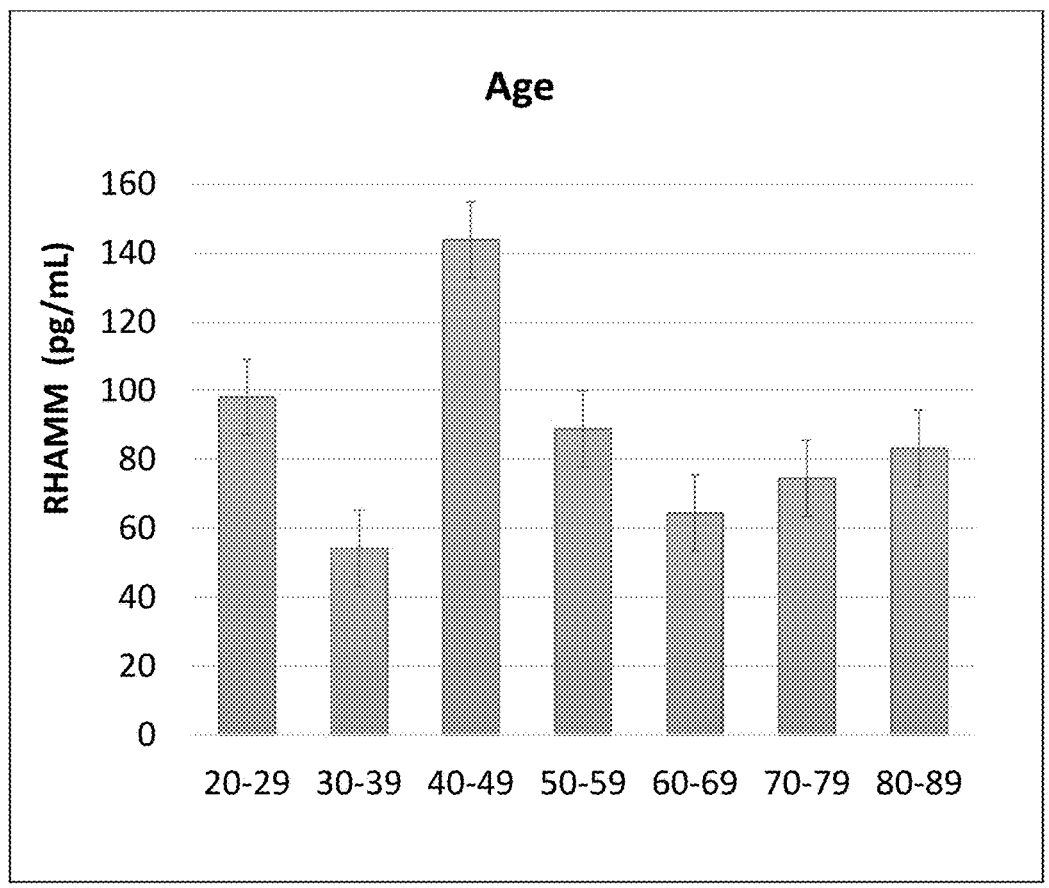
FIG. 5. Urinary RHAMM expression is not different in OC subjects of different ages. Urine from OC subjects with the ages in range 20-29 (n=2), 30-39 (n=5), 40-49 (n=9), 50-59 (n=27), 60-69 (n=31), 70-79 (n=20), 80-89 (n=11) was analyzed for RHAMM levels.
Figure 6:
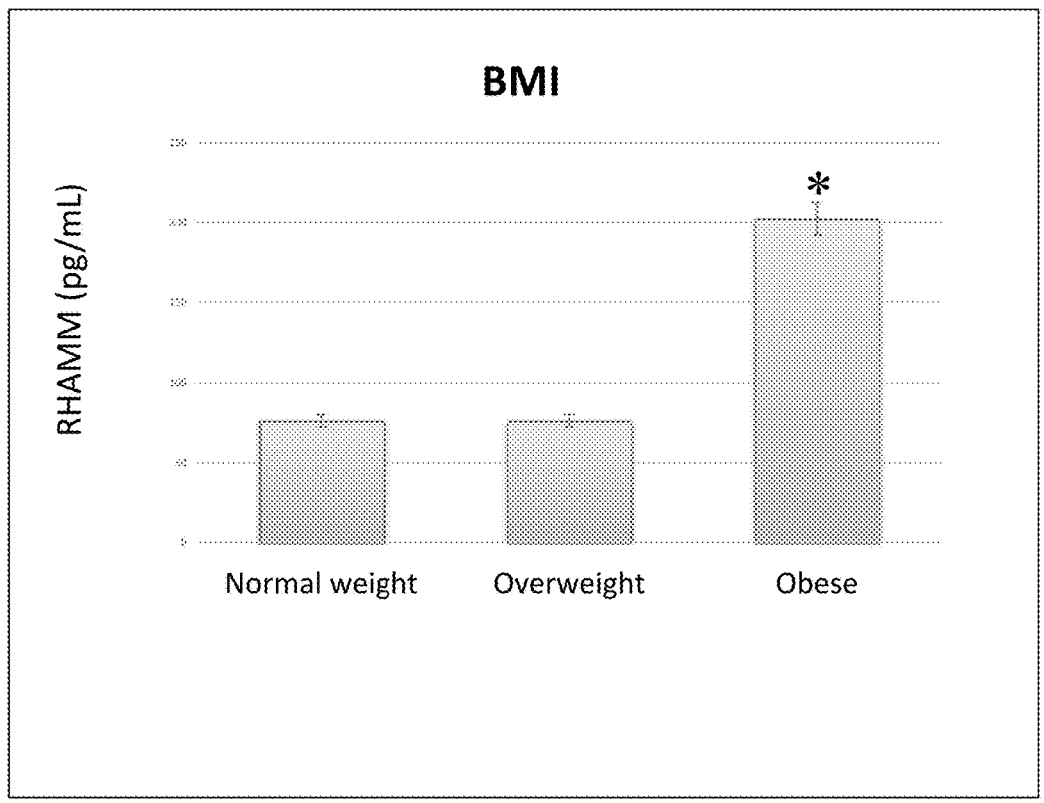
FIG. 6. Urinary RHAMM expression is higher in obese (BMI>30) OC subjects compared to urine from overweight and normal weight OC subjects (BMI<30). BMI>30 (n=9), BMI 25-29.9 (n=4); BMI 18.5-24.9 (n=9). *indicates $p<0.05$.
Figure 7:
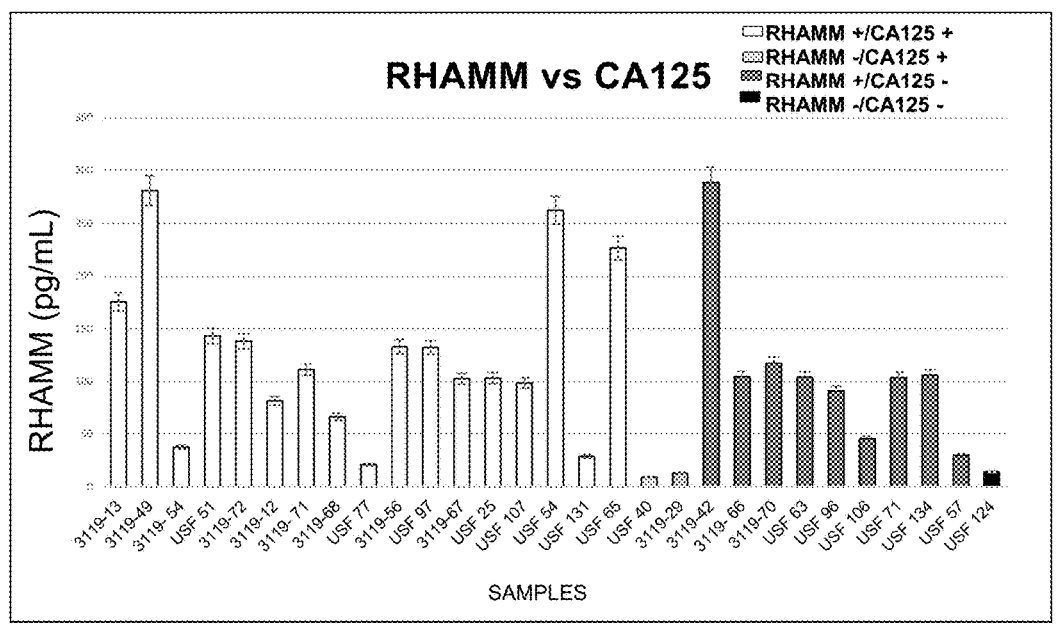
FIG. 7. OC detection rate increases when urinary RHAMM levels are combined with serum CA125 levels.

RHAMM is an itinerant protein with dualistic function. Intracellularly, RHAMM is involved in microtubule spindle assembly and contributes to cell cycle progression. On the extracellular surface, RHAMM is a receptor for Hyaluronan, and activates the ERK½ cell signaling pathway that promotes migration, invasion, and cell proliferation. Although minimal expression of RHAMM is detected in normal tissues, RHAMM is overexpressed in breast and prostate cancers.

The invention provides that RHAMM levels are elevated in urine samples from subjects having OC, CC, or CRC. Accordingly, the invention provides materials and methods for identifying OC, CC, or CRC based on RHAMM levels in a urine sample from a subject. The methods of the invention facilitate detection of OC, CC, or CRC in early stages of the disease where the disease is confined to a tissue. Early detection of a cancer based on the methods described herein facilitates efficient treatment of the cancer, for example, by surgical removal of the diseased tissue. Early detection also reduces medical costs and improves survival.

Another embodiment of the invention provides materials and methods for monitoring the efficacy of a treatment of OC, CC, or CRC based on RHAMM levels in urine samples obtained from a subject before and after the treatment. For example, reduction in the level of RHAMM in a urine sample obtained from a subject that received a treatment can be used to identify the treatment as successful; whereas, unchanged or increased level of RHAMM in a urine sample obtained from a subject that received a treatment can be used to identify the treatment as unsuccessful.

Accordingly, one embodiment of the invention provides a method for identifying OC, CC, or CRC in a subject, the method comprising the steps of:

(a) determining the level of RHAMM in:
  i) a test urine sample obtained from the subject, and
  ii) optionally, a control sample;

(b) optionally, obtaining a reference value for the level of RHAMM; and (c) identifying OC, CC, or CRC in the subject based on the level of RHAMM in the test urine sample and optionally administering a therapy to the subject to treat OC, CC, or CRC; or (d) identifying an absence of OC, CC, or CRC in the subject based on the level of RHAMM in the test urine sample and withholding the therapy to the subject to treat OC, CC, or CRC.

Various techniques are known to a person of ordinary skill in the art to determine the level of RHAMM protein in a sample. Non-limiting examples of such techniques include Western blot analysis, mass spectrometry, ELISA, and radio-immune assay (MA). Methods of performing these techniques are routine in the art. Additional methods of determining the level of RHAMM protein in a sample are also known to a person of ordinary skill in the art and such embodiments are within the purview of the invention.

To practice the methods described herein for identifying a subject as having OC, CC, or CRC, a control sample can be obtained from one or more of the following:

a) an individual belonging to the same species as the subject and not having OC, CC, or CRC, b) an individual belonging to the same species as the subject and having OC, CC, or CRC, c) the subject prior to having OC, CC, or CRC, or d) a solution containing a known concentration of RHAMM, particularly, about 0 to 15 pg/ml, between about 60 pg/ml to about 80 pg/ml, or above 100 pg/ml.

Additional examples of control samples are well known to a person of ordinary skill in the art and such embodiments are within the purview of the current invention.

The reference value for the level of RHAMM protein indicates the level of RHAMM protein in a urine sample obtained from subjects that do not have OC, CC, or CRC or from subjects that have OC, CC, or CRC. As such, the reference value corresponding to level of RHAMM in a urine sample may indicate the absence or presence of OC, CC, or CRC. A reference value associated with the absence of OC, CC, or CRC may be determined based on samples obtained from subjects free from OC, CC, or CRC. A reference value associated with the presence of OC, CC, or CRC may be obtained based on samples obtained from subjects having OC, CC, or CRC.

In one embodiment, the reference value associated with the absence of OC is between 0 to 15 pg/ml of urine; whereas, the reference value associated with the presence of OC is between about 100 pg/ml to about 120 pg/ml of urine. An embodiment of the invention provides a method for determining the RHAMM level in a urine sample of a subject being higher or lower than about 100 pg/ml of urine.

Accordingly, an embodiment of the invention provides determining the level of RHAMM in the urine sample of the subject and determining the level of RHAMM in the urine sample of the subject being above or below a predetermined threshold. In an embodiment, the predetermined threshold of RHAMM is 100 pg/ml of urine.

In another embodiment, the reference value associated with the absence of CC or CRC is between 0 to 15 pg/ml of urine; whereas, the reference value associated with the presence of CC or CRC is between 60 pg/ml to about 80 pg/ml of urine. Accordingly, an embodiment of the invention provides a method for determining the RHAMM level in a urine sample of a subject being between 60 pg/ml to 80 pg/ml of urine.

An embodiment of the invention provides a method for determining the RHAMM level in a urine sample of a subject being between 60 pg/ml to 80 pg/ml of urine.

Accordingly, an embodiment of the invention provides a method for determining the level of RHAMM in the urine sample of the subject and determining the level of RHAMM in the urine sample of the subject being within a predetermined range. In an embodiment, the predetermined range of RHAMM is 60 pg/ml to 80 pg/ml of urine.

The step of identifying a subject as having OC, CC, or CRC is based on the level of RHAMM in a urine sample obtained from a subject. For example, if the level RHAMM in a test urine sample is significant higher than the level RHAMM in a control sample or a reference value that indicates the absence of OC, CC, or CRC, the subject is identified as having OC, CC, or CRC. Similarly, if the level RHAMM in a test urine sample is not significantly higher than the level RHAMM in a control sample or a reference value that indicates the absence of OC, CC, or CRC, the subject is identified as not having OC, CC, or CRC.

On the other hand, if the level of RHAMM in a test urine sample is not significantly lower than the level of RHAMM in a control sample or a reference value that indicates the presence of OC, CC, or CRC, the subject is identified as having OC, CC, or CRC; whereas, if the level of RHAMM in a test urine sample is significantly lower than the level of RHAMM in a control sample or a reference value that indicates the presence of OC, CC, or CRC, the subject is identified as not having OC, CC, or CRC.

Once a subject is identified as having OC, CC, or CRC based on the methods described herein, the step of treating OC, CC, or CRC includes one, two, three or more of:

i) surgery, ii) chemotherapy in combination with radiotherapy, for example, cisplatin, cisplatin plus fluorouracil, or mitomycin in combination with radiotherapy;

iii) chemotherapy without radiotherapy;

iv) radiation alone or in combination with surgery or chemotherapy; and v) immunotherapy.

A further embodiment of the invention provides a method for monitoring the efficacy of a treatment for OC, CC, or CRC. A method for monitoring the efficacy of a treatment for OC, CC, or CRC comprises the steps of:

(a) determining the level of RHAMM in:

i) a pre-treatment test urine sample obtained from the subject before the treatment, ii) a post-treatment test urine sample obtained from the subject after the treatment, and ii) optionally, a control sample;

(b) optionally, a reference value for the level of RHAMM before or after the treatment; and (c) identifying the treatment for OC, CC, or CRC as effective based on the levels of RHAMM in the post-treatment test urine sample compared to the level of RHAMM in the pre-treatment test urine sample and optionally continuing the treatment for OC, CC, or CRC, or (d) identifying the treatment for OC, CC, or CRC as ineffective based on the levels of RHAMM in the post-treatment test urine sample compared to the level of RHAMM in the pre-treatment test urine sample and optionally modifying the treatment for OC, CC, or CRC.

The techniques for determining the level or RHAMM, the control samples, and the reference values discussed above in connection with the methods for identifying OC, CC, or CRC in a subject are also applicable to the methods of monitoring the effect of a treatment for OC, CC, or CRC described herein.

The step of identifying the treatment for OC, CC, or CRC as ineffective utilizes the level of RHAMM in the post-treatment test urine sample and pre-treatment test urine sample. An effective treatment for OC, CC, or CRC is indicated by a decrease in the level of RHAMM in a post-treatment test urine sample compared to a pre-treatment test urine sample. As such, an effective treatment for OC, CC, or CRC decreases the level RHAMM in the urine of a subject having OC, CC, or CRC to the level that is found in the urine of a subject who does not have OC, CC, or CRC. For example, the level of RHAMM in a post-treatment urine sample of a subject significantly below 100 pg/ml indicates that the treatment for OC is effective. Similarly, the level of RHAMM in a post-treatment urine sample of a subject significantly below 60 pg/ml indicates that the treatment for CC or CRC is effective.

Conversely, an ineffective treatment for OC, CC, or CRC is indicated by no decrease in the levels of RHAMM in a post-treatment test urine sample compared to the pre-treatment test urine sample.

As such, the invention provides that RHAMM levels in urine manifests effective or ineffective treatment of OC, CC, or CRC.

Further embodiments of the invention provide diagnostic devices for assaying urinary RHAMM level. The diagnostic devices and assays described herein can be used to diagnose OC, CC, or CRC in a subject. In one embodiment, the diagnostic device is a point-of-care diagnostic device or an enzyme-linked immunosorbent assay (ELISA) apparatus. ELISA apparatus comprises a plate comprising wells having a coating of an antibody or an antigen binding fragment of antibody against RHAMM, and optionally secondary antibodies and other reagents for performing ELISA.

In certain embodiments, the diagnostic devices comprise a control that indicates the highest level of RHAMM present in the urine of a subject that does not have OC, CC, or CRC. In another embodiment, the diagnostic devices comprise a control that indicates the lowest level of RHAMM present in the urine of a subject that has OC, CC, or CRC. Accordingly, an embodiment of the invention provides a diagnostic device for OC that comprises a control that indicates RHAMM in a urine sample at a concentration of about 90 pg/ml, which is the highest level of RHAMM in a urine of a subject that does not have OC. Another embodiment of the invention provides a diagnostic device for OC that comprises a control that indicates RHAMM in a urine sample at a concentration of about 120 pg/ml, which is the lowest level of RHAMM that can be present in the urine of a subject having OC. An example of a diagnostic device is a dipstick device having a control spot or area indicating the recited concentrations of RHAMM in a urine sample.

Also, an embodiment of the invention provides a diagnostic device for CC or CRC that comprises a control that indicates RHAMM in urine sample at a concentration of about 50 pg/ml, which is the highest level of RHAMM present in the urine of a subject that does not have CC or CRC. Another embodiment of the invention provides a diagnostic device for CC or CRC that comprises a control that indicates RHAMM in urine sample at a concentration of about 60 pg/ml, which is the lowest level of RHAMM that can be present in the urine of a subject that has CC or CRC. An example of a diagnostic device is a dipstick device having a control spot or area indicating the recited concentrations of RHAMM in a urine sample.

The invention also provides materials and methods for identifying OC in a subject based on RHAMM level in a urine sample and CA125 level in a blood sample of a subject. The blood sample used herein can be raw blood or blood processed to separate serum or plasma. Accordingly, the term "blood sample" includes a sample of raw blood, serum, or plasma.

Another embodiment of the invention provides materials and methods for monitoring the efficacy of a treatment of OC in a subject based on RHAMM levels in the urine samples obtained from a subject before and after the treatment and CA125 levels in the blood samples obtained from the subject before and after the treatment. For example, decrease in the level of RHAMM in a urine sample of a subject and decrease in the level of CA125 in a blood sample of the subject after receiving a treatment can be used to identify the treatment as successful; whereas, no decrease in the level of RHAMM in a urine sample of a subject and no decrease in the level of CA125 in a blood sample of the subject after receiving a treatment can be used to identify the treatment as unsuccessful.

Accordingly, one embodiment of the invention provides a method for identifying OC in a subject, the method comprising:
(a) determining the level of RHAMM in:
    i) a test urine sample obtained from the subject, and
    ii) optionally, a first control sample;
(b) determining the level of CA125 in:
    i) a test blood sample obtained from the subject, and
    ii) optionally, a second control sample;
(c) optionally, obtaining a first reference value corresponding to the level of RHAMM and/or a second reference value corresponding to the level of CA125; and
(d) identifying OC in the subject based on the level of RHAMM in the test urine sample and the level of CA125 in the test blood sample, and optionally administering a therapy to the subject to treat OC, or
(e) identifying an absence of OC in the subject based on the level of RHAMM in the test urine sample and the level of CA125 in the test blood sample, and withholding the therapy to the subject to treat OC.

Various techniques for determining the level of RHAMM protein and various control samples described above in connection with the methods of identifying OC, CC, or CRC in a subject are also applicable to the methods of identifying OC and such embodiments are within the purview of the invention.

The reference values for the levels of RHAMM or CA125 proteins indicate the level of RHAMM protein in a urine sample or CA125 protein in a blood sample obtained from subjects that do not have OC or from subjects that have OC. As such, the reference value for the level of RHAMM in a urine sample or CA125 in a blood sample may indicate the absence or presence of OC. A reference value indicating the absence of OC may be determined based on samples obtained from subjects known to be free of OC. A reference value indicating the presence of OC may be determined based on samples obtained from subjects having OC.

In one embodiment, the reference value for the level of RHAMM indicating the absence of OC is between 0 to 15 pg/ml of urine; whereas, the reference value indicating the presence of OC is higher than about 100 pg/ml of urine. The reference value of CA125 indicating the absence of OC is between 0 to 15 U/ml of blood; whereas, the reference value indicating the presence of OC is higher than about 65 U/ml of blood.

An embodiment of the invention provides a method for determining the RHAMM level in a urine sample of a subject being higher than about 100 pg/ml and CA125 level in a blood sample of the subject being higher than about 65 U/ml.

Accordingly, an embodiment of the invention provides a method for determining the level of RHAMM in a urine sample of a subject and the level of CA125 in a blood sample of the subject; and determining the level of RHAMM in the urine sample of the subject being above or below a first predetermined threshold and determining the level of CA125 in the blood sample of the subject being above or below a second predetermined threshold. In an embodiment, the first predetermined threshold for RHAMM is 100 pg/ml of urine and the second predetermined threshold for CA125 is 65 U/ml of blood.

The step of identifying a subject as having OC is based on the level of RHAMM in the urine sample obtained from the subject and the level of CA125 in the blood sample obtained from the subject. For example, if the level of RHAMM in the test urine sample and the level of CA125 in the test blood sample are significant higher than the level RHAMM and CA125 in the control samples or the reference values that indicate the absence of OC, the subject is identified as having OC. Similarly, if the level of RHAMM in the test urine sample and the level of CA125 in the test blood sample are not significantly higher than the levels of RHAMM and CA125 in the control samples or the reference values that indicate the absence of OC, the subject is identified as not having OC.

On the other hand, if the level RHAMM in the test urine sample and the level of CA125 in the test blood sample are not significantly lower than the levels RHAMM and CA125 in the control samples or the reference values that indicate the presence of OC, the subject is identified as having OC; whereas, if the level RHAMM in the test urine sample and the level of CA125 in the test blood sample are significantly lower than the levels of RHAMM and CA125 in the control samples or the reference values that indicate the presence of OC, the subject is identified as not having OC.

Once a subject is identified as having OC based on the methods described herein, the step of treating OC includes one or more of:
  i) surgery,
  ii) chemotherapy in combination with radiotherapy, for example, cisplatin, cisplatin plus fluorouracil, or mitomycin in combination with radiotherapy;
  iii) chemotherapy without radiotherapy;
  iv) radiation alone or in combination with surgery or chemotherapy; and
  v) immunotherapy.

A further embodiment of the invention provides a method for monitoring the efficacy of a treatment for OC in a subject. A method for monitoring the efficacy of a treatment for OC in a subject comprises the steps of:
  (a) determining the level of RHAMM in:
    i) a pre-treatment test urine sample obtained from the subject before the treatment,
    ii) a post-treatment test urine sample obtained from the subject after the treatment, and
    iii) optionally, a first control sample;
  (b) determining the level of CA125 in:
    i) a pre-treatment test blood sample obtained from the subject before the treatment,
    ii) a post-treatment test blood sample obtained from the subject after the treatment, and
    iii) optionally, a second control sample;
  (c) optionally, obtaining a first reference value corresponding to level of RHAMM before or after the treatment and a second reference value corresponding to the level of CA125 before or after the treatment; and
  (d) identifying the treatment for OC as effective based on the level of RHAMM in the post-treatment test urine sample compared to the level of RHAMM in the pre-treatment test urine sample and the level of CA125 in the post-treatment test blood sample compared to the level of CA125 in the pre-treatment test blood sample and optionally, continuing the treatment for OC to the subject, or
  (e) identifying the treatment for OC as ineffective based on the level of RHAMM in the post-treatment test urine sample compared to the level of RHAMM in the pre-treatment test urine sample and the level of CA125 in the post-treatment test blood sample compared to the level of CA125 in the pre-treatment test blood sample and optionally, modifying the treatment for OC.

The techniques for determining the level or RHAMM and CA125, the control samples, and the reference values discussed above in connection with the methods for identifying OC in a subject are also applicable to the methods of monitoring the efficacy of a treatment for OC.

The step of identifying the treatment for OC as effective or ineffective is based on the level of RHAMM in the post-treatment test urine sample and pre-treatment test urine sample and the level of CA125 in the post-treatment test blood sample and pre-treatment test blood sample. An effective treatment for OC is indicated by a decrease in the level of RHAMM in a post-treatment test urine sample when compared to a pre-treatment test urine sample and a decrease in the level of CA125 in a post-treatment test blood sample when compared to a pre-treatment test blood sample. As such, an effective treatment for OC decreases the level RHAMM in the urine of a subject having OC to the level that is found in a subject who does not have OC and also decreases the level of CA125 in the blood of a subject having OC to the level that is found in a subject who does not have OC. For example, the level of RHAMM in a post-treatment urine sample of a subject significantly below 100 pg/ml and the level of CA125 in a post-treatment blood sample of the subject significantly below 65 U/ml indicate that the treatment for OC is effective.

Conversely, an ineffective treatment is indicated by no decrease in the level of RHAMM in a post-treatment test urine sample when compared to the pre-treatment test urine sample and no decrease in the level of CA125 in a post-treatment test blood sample when compared to the pre-treatment test blood sample.

As such, the invention provides that RHAMM levels in urine and CA125 level in blood manifests effective or ineffective treatment of OC.

A further embodiment of the invention provides an assay for determining the level RHAMM in a urine sample obtained from a subject and the level of CA125 in a blood sample obtained from the subject.

Further embodiments of the invention provide diagnostic devices for assaying urinary RHAMM level and blood CA125 level. The diagnostic devices and assays described herein can be used to diagnose OC in a subject. In one embodiment, the diagnostic device is an ELISA apparatus or a point-of-care diagnostic device.

ELISA apparatus comprises a plate comprising wells having a coating of an antibody or an antigen binding fragment of antibody against RHAMM and an antibody or an antigen binding fragment of antibody against CA125, and optionally, secondary antibodies against the antibodies against RHAMM and CA125 and other reagents for performing ELISA.

In one embodiment, the ELISA apparatus comprises an ELISA plate comprising a well having a coating of an antibody or an antigen binding fragment of antibody against RHAMM and an antibody or an antigen binding fragment of antibody against CA125. The ELISA apparatus can further comprise a secondary antibody against the antibody or the antigen binding fragment of antibody against RHAMM that is conjugated to a first detectable label and a secondary antibody against the antibody or the antigen binding fragment of antibody against CA125 that is conjugated to a second detectable label. Non-limiting examples of detectable labels include an enzymatic label, fluorescent label, radiolabel, or chemiluminescent label. The signal produced by the first and the second label are distinguishable from each other and depending upon the signal of the first and the second label, the levels of RHAMM and CA125 can be determined in a single well.

In one embodiment, the ELISA apparatus comprises an ELISA plate comprising a first well having a coating of an antibody or an antigen binding fragment of antibody against RHAMM and a second well having a coating of an antibody or an antigen binding fragment of antibody against CA125. The ELISA apparatus can further comprise a secondary antibody against the antibody or the antigen binding fragment of antibody against RHAMM and a secondary antibody against the antibody or the antigen binding fragment of antibody against CA125. In one embodiment, same secondary antibody is used against the antibody or antigen binding fragment against RHAMM and the antibody or antigen binding fragment against CA125. The secondary antibody can be conjugated with a detectable label. Non-limiting examples of detectable labels include an enzymatic label, fluorescent label, radiolabel, or chemiluminescent label.

Certain embodiments of the invention provide a point of care diagnostic devices for OC. In one embodiment, the diagnostic device comprises a first sample receiver for a urine sample and a second sample receiver for a blood sample.

In one embodiment, the diagnostic device comprises a first control that indicates the highest urinary level of RHAMM present in a subject that does not have OC and a second control that indicates the highest blood level of CA125 present in a subject that does not have OC. In another embodiment, the diagnostic device comprises a first control that indicates the lowest urinary level of RHAMM present in a subject that has OC and a second control that indicates the lowest blood level of CA125 present in a subject that has OC.

Accordingly, an embodiment of the invention provides a diagnostic device for OC that comprises a first control that indicates RHAMM in urine of a subject at a concentration of about 90 pg/ml, which is the highest level of RHAMM in urine of a subject that does not have OC and a second control that indicates CA125 in blood of a subject at a concentration of about 15 U/ml, which is the highest level of CA125 in blood of a subject that does not have OC. Another embodiment of the invention provides a diagnostic device for OC that comprises a first control that indicates RHAMM in the urine of a subject at a concentration of about 120 pg/ml, which is the lowest level of RHAMM in the urine of a subject that has OC and a second control that indicates CA125 in blood of a subject at a concentration of about 65 U/ml, which is the lowest level of CA125 in the blood of a subject that has OC.

In another embodiment, the diagnostic device is a kit containing reagents for assaying urinary RHAMM level and blood CA125 level. In one embodiment, the kit comprises an antibody or the antigen binding fragment of antibody against RHAMM and an antibody or the antigen binding fragment of antibody against CA125. The kit can also comprise one or more secondary antibodies against the antibodies against RHAMM and CA125. The kits can further comprise a control sample for RHAMM and a control sample for CA125.

In one embodiment, a control sample for RHAMM contains RHAMM at a concentration of about 90 pg/ml, which is the highest level of RHAMM in the urine of a subject that does not have OC. In another embodiment, a control sample for RHAMM contains RHAMM at a concentration of about 120 pg/ml, which is the lowest level of RHAMM in the urine of a subject that has OC. In a further embodiment, a control sample for CA125 contains CA125 at a concentration of about 15 U/ml, which is the highest level of CA125 in the blood of a subject that does not have OC. In an even further embodiment, a control for CA125 contains CA125 at a concentration of about 65 U/ml, which is the lowest level of CA125 in the blood of a subject that has OC.

The kits of the invention can further comprise reagents for treating the samples, for example, for removal of impurities and other constituents that are not assayed.

As such, the invention provides the following embodiments: Embodiment 1. A method of identifying ovarian cancer (OC), cervical cancer (CC), or colorectal cancer (CRC) in a subject, the method comprising the steps of:
(a) determining the level of RHAMM in:
i) a test urine sample obtained from the subject, and
ii) optionally, a control sample;
(b) optionally, obtaining a reference value for the level of RHAMM; and
(c) identifying OC, CC, or CRC in the subject based on the level of RHAMM in the test urine sample and optionally, administering a therapy to the subject to treat OC, CC, or CRC, or
(d) identifying an absence of OC, CC, or CRC in the subject based on the level of RHAMM in the test urine sample and withholding the therapy to the subject to treat OC, CC, or CRC.

Embodiment 2. The method of embodiment 1, wherein the reference value for the level of RHAMM:
i) indicates the absence of OC, CC, or CRC and is between 0 to 15 pg/ml of urine,
ii) indicates the presence of OC is between about 100 pg/ml to about 120 pg/ml of urine,
iii) indicates the presence of CC or CRC and is between 60 pg/ml to about 100 pg/ml of urine.

Embodiment 3. The method of embodiment 1, the method further comprising administering a treatment to a subject identified as having OC, CC, or CRC; the treatment comprising one or more of:
i) a surgery,
ii) a chemotherapy in combination with a radiotherapy,
iii) the chemotherapy without the radiotherapy,
iv) the radiotherapy alone or in combination with the surgery or chemotherapy, and
v) an immunotherapy.

Embodiment 4. A method for monitoring the effect of a treatment for OC, CC, or CRC in a subject, the method comprising the steps of:
(a) determining the level of RHAMM in:
i) a pre-treatment test urine sample obtained from the subject before the treatment, ii) a post-treatment test urine sample obtained from the subject after the treatment, and
iii) optionally, a control sample;
(b) optionally, a reference value for the level of RHAMM before or after the treatment; and
(c) identifying the treatment for OC, CC, or CRC as effective based on the level of RHAMM in the post-treatment test urine sample compared to the level of RHAMM in the pre-treatment test urine sample and optionally, continuing the treatment for OC, CC, or CRC, or
(d) identifying the treatment for OC, CC, or CRC as ineffective based on the level of RHAMM in the post-treatment test urine sample compared to the level of RHAMM in the pre-treatment test urine sample and optionally, modifying the treatment for OC, CC, or CRC.

Embodiment 5. The method of embodiment 4, wherein the reference value for the level of RHAMM after the treatment:
i) indicates the treatment as effective and is between 0 to 15 pg/ml of urine,
ii) indicates the treatment as ineffective for OC and is between about 100 pg/ml to about 120 pg/ml of urine,
iii) indicates the treatment as ineffective for CC or CRC and is between 60 pg/ml to about 100 pg/ml of urine.

Embodiment 6. A method for identifying OC in a subject, the method comprising:
(a) determining the level of RHAMM in:
i) a test urine sample obtained from the subject, and
ii) optionally, a first control sample;
(b) determining the level of CA125 in:
i) a test blood sample obtained from the subject, and
ii) optionally, a second control sample;
(c) optionally, obtaining a first reference value corresponding to the level of RHAMM and/or a second reference value corresponding to the level of CA125; and
(d) identifying OC in the subject based on the level of RHAMM in the test urine sample and the level of CA125 in the test blood sample, and optionally, administering a therapy to the subject to treat OC, or
(e) identifying an absence of OC in the subject based on the level of RHAMM in the test urine sample and the level of CA125 in the test blood sample, and withholding the therapy to the subject to treat OC.

Embodiment 7. The method of embodiment 6,
wherein the reference value for the level of RHAMM:
i) indicates the absence of OC and is between 0 to 15 pg/ml of urine,
ii) indicates the presence of OC and is between about 100 pg/ml to about 120 pg/ml of urine;
and wherein the reference value for the level of CA125:
i) indicates the absence of OC and is between 0 to 15 U/ml of blood,
ii) indicates the presence of OC and is about 65 U/ml of blood.

Embodiment 8. The method of embodiment 6, the method further comprising administering a treatment to a subject identified as having OC; the treatment comprising one or more of:
i) a surgery,
ii) a chemotherapy in combination with a radiotherapy,
iii) the chemotherapy without the radiotherapy,
iv) the radiotherapy alone or in combination with the surgery or chemotherapy, and
v) an immunotherapy.

Embodiment 9. A method for monitoring the effect of a treatment for OC in a subject, the method comprising the steps of:
(a) determining the level of RHAMM in:
i) a pre-treatment test urine sample obtained from the subject before the treatment,
ii) a post-treatment test urine sample obtained from the subject after the treatment, and
iii) optionally, a first control sample;
(b) determining the level of CA125 in:
i) a pre-treatment test blood sample obtained from the subject before the treatment,
ii) a post-treatment test blood sample obtained from the subject after the treatment, and
iii) optionally, a second control sample;
(c) optionally, obtaining a first reference value corresponding to level of RHAMM before or after the treatment and/or a second reference value corresponding to the level of CA125 before or after the treatment; and
(d) identifying the treatment for OC as effective based on the level of RHAMM in the post-treatment test urine sample compared to the level of RHAMM in the pre-treatment test urine sample and the level of CA125 in the post-treatment test blood sample compared to the level of CA125 in the pre-treatment test blood sample and optionally, continuing the treatment for OC to the subject, or
(e) identifying the treatment for OC as ineffective based on the level of RHAMM in the post-treatment test urine sample compared to the level of RHAMM in the pre-treatment test urine sample and the level of CA125 in the post-treatment test blood sample compared to the level of CA125 in the pre-treatment test blood sample and optionally, modifying the treatment for OC.

Embodiment 10. The method of embodiment 9, wherein:
i) the reference value for the level of RHAMM after the treatment:
a) indicates the treatment as effective and is between 0 to 15 pg/ml of urine,
b) indicates the treatment as ineffective and is between about 100 pg/ml to about 120 pg/ml of urine; and
ii) the reference value for the level of CA125 after the treatment:
a) indicates the treatment as effective and is between 0 to 15 U/ml of blood,
b) indicates the treatment as ineffective and is about 65 U/ml of blood.

Embodiment 11. A device for assaying urinary RHAMM level and blood CA125 level, the device comprising:
i) an ELISA plate comprising:
a) a well having a coating of: an antibody or an antigen binding fragment of antibody against RHAMM and an antibody or an antigen binding fragment of antibody against CA125,
b) a secondary antibody against the antibody or the antigen binding fragment of antibody against RHAMM conjugated to a first detectable label and a secondary antibody against the antibody or the antigen binding fragment of antibody against CA125 conjugated to a second detectable label; or
ii) an ELISA plate comprising:
a) a first well having a coating of an antibody or an antigen binding fragment of antibody against RHAMM and a second well having a coating of an antibody or an antigen binding fragment of antibody against CA125, and
b) a secondary antibody against the antibody or the antigen binding fragment of antibody against RHAMM and a secondary antibody against the antibody or the antigen binding fragment of antibody against CA125.

Embodiment 12. A diagnostic device comprising:
i) a first sample receiver for a urine sample and a second sample receiver for a blood sample, and
ii) a first control for the level of RHAMM and a second control for the level of CA125.

Embodiment 13. The diagnostic device of embodiment 12, wherein:
i) the first control indicates the highest urinary level of RHAMM present in a subject that does not have OC and the second control indicates the highest blood level of CA125 present in a subject that does not have OC; or
ii) the first control indicates the lowest urinary level of RHAMM present in a subject that has OC and the second control indicates the lowest blood level of CA125 present in a subject that has OC.

Embodiment 14. The diagnostic device of embodiment 12, wherein:
i) the first control for RHAMM contains RHAMM at a concentration of about 90 pg/ml of urine and the second control for CA125 contains CA125 at a concentration of about 15 U/ml of blood; or
ii) the first control for RHAMM contains RHAMM at a concentration of about 120 pg/ml of urine and the second control for CA125 contains CA125 at a concentration of about 65 U/ml of blood.

Embodiment 15. A method for determining the level of RHAMM in a urine sample of a subject being above or below a predetermined threshold, the method comprising the steps of determining the level of RHAMM in the urine sample of the subject and determining the level of RHAMM in the urine sample of the subject being above or below the predetermined threshold.

Embodiment 16. The method of embodiment 15, wherein the predetermined threshold of RHAMM is:
i) between 0 to 15 pg/ml of urine,
ii) between 60 pg/ml to about 100 pg/ml of urine, or
iii) 100 pg/ml of urine.

Embodiment 17. A method for determining the level of RHAMM in a urine sample of a subject being above or below a first predetermined threshold and determining the level of CA125 in a blood sample of a subject being above or below a second predetermined threshold, the method comprising the steps of determining the level of RHAMM in the urine sample of the subject and the level of CA125 in blood sample of a subject; and determining the level of RHAMM in the urine sample of the subject being above or below the first predetermined threshold and determining the level of CA125 in the blood sample of the subject being above or below the second predetermined threshold.

Embodiment 18. The method of embodiment 17, wherein:
i) the first predetermined threshold for RHAMM is:
a) between 0 to 15 pg/ml of urine, or
b) 100 pg/ml of urine; and
ii) the second predetermined threshold for CA125 is:
a) between 0 to 15 U/ml of blood, or
b) 65 U/ml of blood.

As used herein, the singular forms "a", "an" and "the" are intended to include the plural forms as well, unless the context clearly indicates otherwise. Further, to the extent that the terms "including", "includes", "having", "has", "with", or variants thereof are used in either the detailed description and/or the claims, such terms are intended to be inclusive in a manner similar to the term "comprising". The transitional terms/phrases (and any grammatical variations thereof) "comprising", "comprises", "comprise", include the phrases "consisting essentially of", "consists essentially of", "consisting", and "consists".

The phrases "consisting essentially of" or "consists essentially of" indicate that the claim encompasses embodiments containing the specified materials or steps and those that do not materially affect the basic and novel characteristic(s) of the claim.

The term "about" means within an acceptable error range for the particular value as determined by one of ordinary skill in the art, which will depend in part on how the value is measured or determined, i.e., the limitations of the measurement system. For example, "about" can mean within 1 or more than 1 standard deviation, per the practice in the art. Alternatively, "about" can mean a range of up to 0-20%, 0 to 10%, 0 to 5%, or up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term "about" meaning within an acceptable error range for the particular value should be assumed. In the context of concentration of biomarkers where the terms "about" is used, the stated amount of the biomarker can be within a variation (error range) of 0-10% around the value ($X \pm 10\%$).

In the present disclosure, ranges are stated in shorthand, so as to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediate ranges encompassed within 0.1-1.0, such as 0.2-0.5, 0.2-0.8, 0.7-1.0, etc.

When ranges are used herein, combinations and subcombinations of ranges (e.g., subranges within the disclosed range), specific embodiments therein are intended to be explicitly included.

"Treatment" or "treating" (and grammatical variants of these terms), as used herein, are used interchangeably. These terms refer to an approach for obtaining beneficial or desired results including but not limited to therapeutic benefit. A therapeutic benefit is achieved with the eradication or amelioration of one or more of the physiological symptoms associated with BC such that an improvement is observed in the subject, notwithstanding that the subject may still be afflicted with BC.

"Subject" refers to an animal, such as a mammal, for example a human. The methods described herein can be useful in both humans and non-human animals. In some embodiments, the subject is a mammal (such as an animal model of disease), and in some embodiments, the subject is human.

All patents, patent applications, provisional applications, and publications referred to or cited herein are incorporated by reference in their entirety, including all figures and tables, to the extent they are not inconsistent with the explicit teachings of this specification.

Materials and Methods

Subject Cohort

Urine samples from male and female healthy controls (n=29), subjects with benign gynecological disease (n=30), subjects with ovarian cancer (n=126), lung cancer (n=20), breast cancer (n=20), brain cancer (n=20), head and neck cancer (n=19), prostate cancer (n=22), cervical cancer (n=21), colorectal cancer (n=9), melanoma (n=20), endometrial cancer (n=20) as well as sarcoma (n=19) were analyzed by ELISA.

Western Blot Analysis on Urine Samples

Normal and OC urine samples were centrifuged at 16,000 rpm using 30,000 Kda microfilter to concentrate the urine specimens. Concentrated urine samples were electrophoresed via 10% SDS-PAGE acrylamide gel and transferred to nitrocellulose membrane. Membranes were blocked for 1 hour at room temperature using 5% milk in Tris-buffer saline with tween. Membranes were then incubated overnight at 4° C. in monoclonal rabbit anti-CD168 RHAMM antibody (ABCAM) and then incubated for 1 hour at room temperature in goat anti-rabbit HRP conjugated antibody and GAPDH was used as a loading control. (Thermo Fisher scientific) Bands were detected using SuperSignal West Femto Substrate (Thermo Fisher Scientific), densitometric analysis was performed using image studio lite software program and normalized to GAPDH.

Human HMMR/CD168/RHAMM Sandwich ELISA

Protocol was performed according to manufacturer's recommendations for urine sample specimens. (LifeSpan BioSciences, Inc.) All samples were thawed to room temperature as per instructions. Results are expressed as the average of duplicate samples +/− standard error. Statistical analysis of data was subjected to descriptive and students T test.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

Example 1—Elevated Rhamm in Urine of Subjects Having OC

Urine was collected from normal healthy volunteers (n=29) and from subjects with OC (n=126), subjects having other cancers (n=175), and subjects with benign gynecologic disease (n=30). Urinary RHAMM levels were measured by ELISA using a commercially available RHAMM ELISA assay (catalog # LS-F11646, LifeSpan BioSciences, Inc., Seattle, Wash.) and the results were expressed as the average pg/ml RHAMM from triplicate samples±SE.

The average amount of RHAMM in the urine samples from ovarian cancer subjects was 116 pg/ml, which was almost 20 times higher than the amount of RHAMM in the urine samples from healthy controls, which was about 6 pg/ml. Also, the average amount of RHAMM in the urine samples from ovarian cancer subjects was almost 10 times higher compared to urinary RHAMM levels from women with benign gynecologic disease, which was about 10 pg/ml.

Elevated urinary RHAMM levels were associated with 90% of ovarian cancers tested (26/29). On the other hand, serum levels of CA125 higher than 65 U/ml only identified 65% of ovarian cancer subjects. As such, the specificity and sensitivity of CA125 as a biomarker for OC are lower than the specificity and sensitivity of urinary RHAMM as a biomarker for OC. Further, combining subjects as either RHAMM+ or CA125+ increased detection of ovarian cancer to 96% (28/29).

Comparison of clinical parameters indicated that urinary levels of RHAMM did not distinguish between ovarian tumor stage and grade or subject age. However, urinary levels of RHAMM were related to increased subject BMI. Lastly, urinary RHAMM levels were also found to be elevated in the urine of subjects with cervical and colorectal cancer, though average urinary RHAMM levels were somewhat less than that found in OC subjects at 71 and 81 pg/ml, respectively.

Therefore, quantification of urinary RHAMM by ELISA-based assays appears to provide a safe, sensitive, specific and economical method to detect ovarian cancer, to monitor ovarian cancer throughout the course of disease and to predict therapeutic and prognostic outcome. Elevated urinary RHAMM levels may also be predictive of cervical and colorectal cancer.

We claim:

1. A kit for assaying RHAMM level and CA125 level, the kit consisting essentially of: a test apparatus and optionally, one or more controls, reagents for assaying RHAMM level and CA125 level, and one or more sample receivers,
   wherein the test apparatus is:
   i) an ELISA
      plate consisting of a well coated with a layer consisting of: an antibody against RHAMM or an antigen binding fragment of antibody against RHAMM and an antibody against CA125 or an antigen binding fragment of antibody against CA125;
   ii) an ELISA
      plate consisting of a first well coated with a layer consisting of an antibody against RHAMM or an antigen binding fragment of antibody against RHAMM and a second well coated with a layer consisting of an antibody against CA125 or an antigen binding fragment of antibody against CA125;
   iii) a point of care diagnostic device consisting of a test surface coated with a layer consisting of an antibody against RHAMM or an antigen binding fragment of antibody against RHAMM and an antibody or an antigen binding fragment of antibody against CA125; or
   iv) a point of care diagnostic device consisting of a test surface consisting of a first test surface and a second test surface, the first test surface coated with a layer consisting of an antibody against RHAMM or an antigen binding fragment of antibody against RHAMM and the second test surface coated with a layer consisting of an antibody against RHAMM or an antigen binding fragment of antibody against CA125.

2. The kit of claim 1, wherein the test apparatus is the ELISA plate, and the one or more controls comprise:
   i) a first RHAMM control that indicates a highest urinary level of RHAMM present in a subject that does not have ovarian cancer (OC) and a first CA125 control that indicates a highest blood level of CA125 present in the subject that does not have OC; and/or
   ii) a second RHAMM control that indicates a lowest urinary level of RHAMM present in a subject that has OC and a second CA125 control that indicates a lowest blood level of CA125 present in a subject that has OC.

3. The kit of claim 2, wherein:
   i) the first RHAMM control has 90 pg/ml of RHAMM and the first CA125 control has 15 U/ml of CA125; and/or ii) the second RHAMM control has 120 pg/ml of RHAMM and the second CA125 control has 65 U/ml of CA125.

4. The kit of claim 1, wherein the test apparatus is the ELISA plate, and the one or more controls consist of:
  i) a first RHAMM control that indicates a highest urinary level of RHAMM present in a subject that does not have OC and a first CA125 control that indicates a highest blood level of CA125 present in the subject that does not have OC; and/or
  ii) a second RHAMM control that indicates a lowest urinary level of RHAMM present in a subject that has OC and a second CA125 control that indicates a lowest blood level of CA125 present in a subject that has OC.

5. The kit of claim 4, wherein the one or more controls consist of:
  i) the first RHAMM control having 90 pg/ml of RHAMM, and the first CA125 control having 15 U/ml of CA125; and/or
  ii) the second RHAMM control having 120 pg/ml of RHAMM, and the second CA125 control having 65 U/ml of CA125.

6. The kit of claim 1, wherein the test apparatus is the point-of-care diagnostic device, and the one or more controls comprise:
  i) a first RHAMM control comprising a first RHAMM area comprising RHAMM at a concentration that indicates the highest urinary level of RHAMM present in a subject that does not have OC and a first CA125 control comprising a first CA125 area comprising CA125 at a concentration that indicates the highest blood level of CA125 present in the subject that does not have OC; and/or
  ii) a second RHAMM control comprising a second RHAMM area comprising RHAMM at a concentration that indicates the lowest urinary level of RHAMM present in a subject that has OC and a second CA125 control comprising a second CA125 area comprising CA125 at a concentration that indicates the lowest blood level of CA125 present in the subject that has OC.

7. The kit of claim 6, wherein:
  i) the first RHAMM area has 90 pg/ml of RHAMM and the first CA125 area has 15 U/ml of CA125; and/or
  ii) the second RHAMM area has 120 pg/ml of RHAMM and the second CA125 area has 65 U/ml of CA125.

8. The kit of claim 1, wherein the test apparatus is the point-of-care diagnostic device, and the one or more controls consist of:
  i) a first RHAMM control consisting of a first RHAMM area consisting of RHAMM at a concentration that indicates the highest urinary level of RHAMM present in a subject that does not have OC and a first CA125 control consisting of a first CA125 area consisting of CA125 at a concentration that indicates the highest blood level of CA125 present in the subject that does not have OC; and/or
  ii) a second RHAMM control consisting of a second RHAMM area consisting of RHAMM at a concentration that indicates the lowest urinary level of RHAMM present in a subject that has OC and a second CA125 control consisting of a second CA125 area consisting of CA125 at a concentration that indicates the lowest blood level of CA125 present in the subject that has OC.

9. The kit of claim 8, wherein:
  i) the first RHAMM area has 90 pg/ml of RHAMM and the first CA125 area has 15 U/ml of CA125; and/or
  ii) the second RHAMM area has 120 pg/ml of RHAMM and the second CA125 area has 65 U/ml of CA125.

10. The kit of claim 1, wherein the test apparatus is: an ELISA plate consisting of a well coated with a layer consisting of: an antibody against RHAMM or an antigen binding fragment of antibody against RHAMM and an antibody against CA125 or an antigen binding fragment of antibody against CA125.

11. The kit of claim 1, wherein the test apparatus is: an ELISA a plate consisting of a first well coated with a layer consisting of an antibody against RHAMM or an antigen binding fragment of antibody against RHAMM and a second well coated with a layer consisting of an antibody against CA125 or an antigen binding fragment of antibody against CA125.

12. The kit of claim 1, wherein the test apparatus is: a point of care diagnostic device consisting of a test surface coated with a layer consisting of an antibody against RHAMM or an antigen binding fragment of antibody against RHAMM and an antibody against CA125 or an antigen binding fragment of antibody against CA125.

13. The kit of claim 1, wherein the test apparatus is: a point of care diagnostic device consisting of a test surface consisting of a first test surface and a second test surface, the first test surface coated with a layer consisting of an antibody against RHAMM or an antigen binding fragment of antibody against RHAMM and the second test surface coated with a layer consisting of an antibody against CA125 or an antigen binding fragment of antibody against CA125.

14. The kit of claim 1, wherein the reagents for assaying RHAMM level and CA125 level comprise secondary antibodies.

15. The kit of claim 1, wherein the kit comprises a urine sample receiver and a blood sample receiver.

16. A method of determining the level of: RHAMM in a urine sample and CA125 in a blood sample, the method comprising the steps of: i) providing the kit of claim 1, and ii) performing an assay to determine the level of: RHAMM in the urine sample and CA125 in the blood sample.

* * * * *